United States Patent
Bayer et al.

(12)
(10) Patent No.: US 6,414,031 B1
(45) Date of Patent: Jul. 2, 2002

(54) BISOXIMETHER DERIVATIVES, METHODS AND INTERMEDIATE PRODUCTS FOR THE PRODUCTION THEREOF, AND THEIR USE FOR COMBATING FUNGICIDAL PESTS AND ANIMAL PESTS

(75) Inventors: Herbert Bayer, Mannheim; Roland Götz, Ludwigshafen; Michael Keil, Freinsheim; Hubert Sauter; Oliver Cullmann, both of Mannheim; Markus Gewehr, Kastellaun; Wassilios Grammenos, Ludwigshafen; Andreas Gypser, Mannheim; Bernd Müller, Frankenthal; Arne Ptock, Ludwigshafen; Eberhard Ammermann, Heppenheim; Thomas Grote, Schifferstadt; Gisela Lorenz, Neustadt; Siegfried Strathmann, Limburgerhof; Volker Harries, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/674,533

(22) PCT Filed: May 4, 1999

(86) PCT No.: PCT/EP99/03003

§ 371 (c)(1),
(2), (4) Date: Nov. 2, 2000

(87) PCT Pub. No.: WO99/59982

PCT Pub. Date: Nov. 25, 1999

(30) Foreign Application Priority Data

May 14, 1998 (DE) .......................... 198 21 604

(51) Int. Cl.[7] .............................................. A01N 37/18
(52) U.S. Cl. .................. 514/619; 560/35; 560/129; 560/157; 562/451; 564/167; 564/166; 558/389; 514/477
(58) Field of Search ............ 560/35, 129, 157; 562/451; 564/167, 166, 619, 477; 514/619, 477; 558/389

(56) References Cited

U.S. PATENT DOCUMENTS 5,194,662 A 3/1993 Brand et al. ............... 560/35
5,298,527 A 3/1994 Grammenos et al. ....... 514/539
5,874,467 A 2/1999 Bayer et al. ............... 514/538
5,889,059 A 3/1999 Bayer et al. ............... 514/619

FOREIGN PATENT DOCUMENTS

| CA | 2 224 887 | | 2/1997 |
|---|---|---|---|
| EP | 254 426 | | 1/1988 |
| EP | 0370 629 | | 5/1990 |
| EP | 463 488 | | 1/1992 |
| EP | 472 300 | | 2/1992 |
| EP | 513 580 | | 11/1992 |
| WO | WO 95/18789 | | 7/1995 |
| WO | WO 95/21153 | * | 8/1995 |
| WO | WO 95/21154 | * | 8/1995 |
| WO | WO 97/05103 | | 2/1997 |

* cited by examiner

Primary Examiner—Paul J. Killos
Assistant Examiner—Héctor Reyes
(74) Attorney, Agent, or Firm—Keil & Weinkauf

(57) ABSTRACT

There are disclosed bisoxime ether derivatives of the formula I

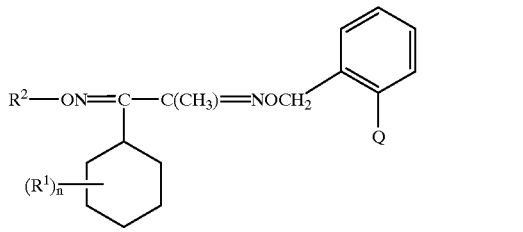

in which the variables have the following meanings:

$R^1$ is halogen, $C_1$–$C_4$-alkyl, $C_1$–$C_4$-haloalkyl, $C_1$–$C_4$-alkoxy or $C_1$–$C_4$-haloalkoxy;

n is 1 to 5, it being possible for the radicals $R^1$ to be different if n is other than 1;

$R^2$ is $C_1$–$C_4$-alkyl, $C_3$–$C_6$-alkenyl or $C_3$–$C_6$-alkynyl, it being possible for these groups to be partially or fully halogenated;

Q is $C(=CHOCH_3)$—$COOCH_3$, $C(=CHCH_3)$—$COOCH_3$, $C(=NOCH_3)$—$COOCH_3$ or $C(=NOCH_3)$ 13 $CONHCH_3$;

and salts thereof, processes and intermediates for the preparation of these compounds, and their use for controlling animal pests and harmful fungi.

17 Claims, No Drawings

BISOXIMETHER DERIVATIVES, METHODS AND INTERMEDIATE PRODUCTS FOR THE PRODUCTION THEREOF, AND THEIR USE FOR COMBATING FUNGICIDAL PESTS AND ANIMAL PESTS

The present invention relates to bisoxime ether derivatives of the formula I

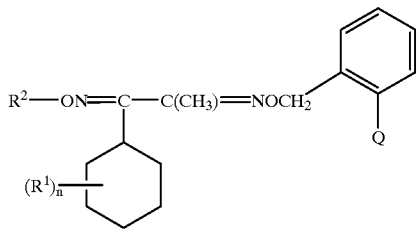

in which the variables have the following meanings:
$R^1$ is halogen, $C_1$–$C_4$-alkyl, $C_1$–$C_4$-haloalkyl, $C_1$–$C_4$-alkoxy or $C_1$–$C_4$-haloalkoxy;
n is 1 to 5, it being possible for the radicals $R^1$ to be different if n is other than 1;
$R^2$ is $C_1$–$C_4$-alkyl, $C_3$–$C_6$-alkenyl or $C_3$–$C_6$-alkynyl, it being possible for these groups to be partially or fully halogenated;
Q is $C(=CHOCH_3)$—$COOCH_3$, $C(=CHCH_3)$—$COOCH_3$, $C(=NOCH_3)$—$COOCH_3$ or $C(=NOCH_3)$—$CONHCH_3$;
and to salts thereof.

Moreover, the invention relates to processes and intermediates for the preparation of these compounds and to their use for controlling animal pests and harmful fungi.

WO-A 95/18789, WO-A 95/21153, WO-A 95/21154 and WO-A 97/05103 disclose bisoxime ether derivatives for controlling harmful fungi and animal pests, but these are not always satisfactory with regard to their action.

It is an object of the present invention to provide novel compounds of this type with an improved action.

We have found that this object is achieved by the bisoxime ether derivatives I defined at the outset. Moreover, we have found processes and intermediates for their preparation, and also compositions comprising them for controlling animal pests and harmful fungi and their use for this purpose.

The compounds of the formula I differ from the compounds mentioned in the publications cited above by the design of the bisoxime ether group, which has attached to it a substituted cyclohexyl group.

The compounds I can be obtained by various routes by processes known per se.

When synthesizing the compounds I, it is, in principle, irrelevant whether it is the group —Q or the group

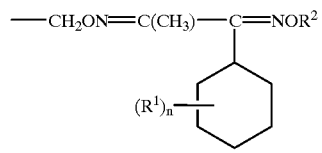

which is constructed first.

The construction of group —Q is disclosed, for example, in the publications mentioned at the outset and in those which follow: EP-A 254 426, EP-A 370 629, EP-A 463 488, EP-A 472 300 and EP-A 513 580.

When synthesizing the compounds I, a procedure is generally followed in which a benzyl derivative of the formula II is reacted with a hydroxyimine of the formula III

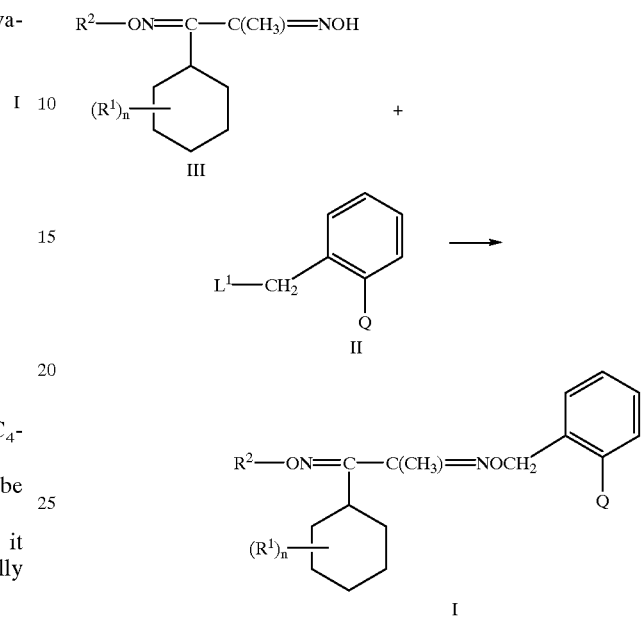

In formula II, $L^1$ is a nucleophilically exchangeable leaving group, for example halogen or sulfonate groups, preferably chlorine, bromine, iodine, mesylate, tosylate or triflate.

The reaction takes place in an inert organic solvent in the presence of a base, for example sodium hydride, potassium hydroxide, sodium hydroxide, sodium methoxide, sodium ethoxide, potassium carbonate or triethylamine, following the methods described in Houben-Weyl, 4th Edition, Vol. E 14b, p. 370 et seq. and ibid. Vol. 10/1, p. 1189 et seq.

The hydroxyimine III required is obtained, for example, by reacting a corresponding dihydroxyimine IV with the compound of the formula VI

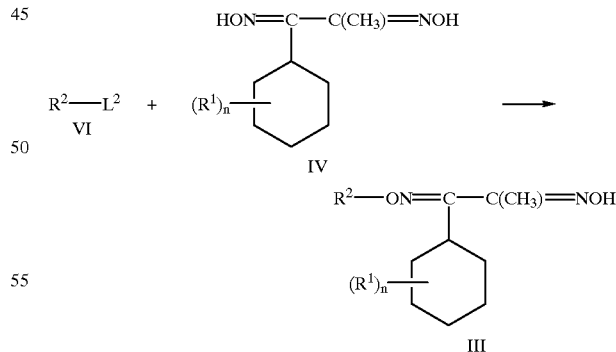

In formula VI, $L^2$ is a nucleophilically exchangeable leaving group, for example halogen or sulfonate groups, preferably chlorine, bromine, iodine, mesylate, tosylate or triflate.

The reaction takes place in an inert organic solvent in the presence of a base, for example potassium carbonate, potassium hydroxide, sodium hydride, sodium hydroxide, sodium methoxide, sodium ethoxide, pyridine or triethylamine as described in: Houben-weyl, 4th Edition, Vol. E 14b, p. 307 et seq., p. 370 et seq. and p. 385 et seq.; ibid., 4th Edition, Vol. 10/4, p. 55 et seq., p. 180 et seq. and p. 217 et seq.; ibid., 4th Edition, Vol. E 5, p. 780 et seq.

The compounds of the formula IV can be prepared by known methods [cf. Gazz. Chim. Ital. 59 (1929), p. 719; Collect. Bull. Soc. Chim. Fr. 17 (1897), p. 71; C. R. Seances Acad. Sci. Ser. D Vol. 267 (1968), p. 579].

Alternatively, the compounds I may also be obtained by first reacting the benzyl derivative II with the dihydroxyimino derivative IV to give a corresponding benzyl oxime of the formula V, V subsequently being reacted with a compound of the formula VI to give I.

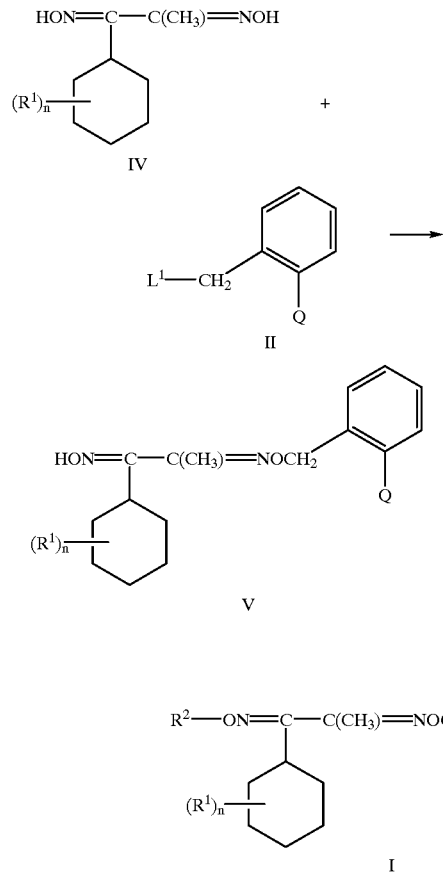

The reaction takes place in an inert organic solvent in the presence of a base, for example potassium carbonate, potassium hydroxide, sodium hydride, sodium hydroxide, sodium methoxide, sodium ethoxide, pyridine or triethylamine in accordance with the methods described in Houben-Weyl, 4th Edition, Vol. 10/1, p. 1189 et seq., Vol. E 14b, p. 307 et seq., p. 370 et seq. and p. 385 et seq., Vol. 10/4, p. 55 et seq., p. 180 et seq. and p. 217 et seq., Vol. E 5, p. 780 et seq.

Similarly, it is also possible to prepare the required hydroxyimine of the formula III from a carbonylhydroxyimine VII by reacting the latter with a hydroxylamine IXa or a salt thereof IXb.

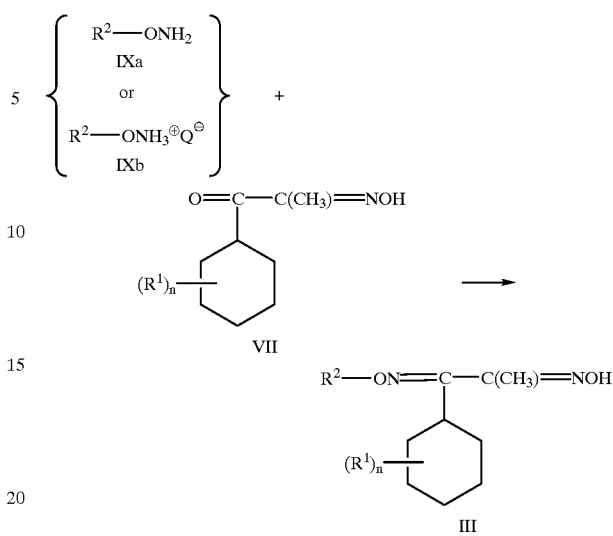

In formula IXb, $Q^{\ominus}$ is the anion of an acid, in particular of an inorganic acid, for example halide, such as chloride.

The reaction takes place in an inert organic solvent in accordance with the methods described in EP-A 513 580 and Houben-Weyl, 4th Edition, Vol. 10/4, p. 73 et seq., Vol. E 14b, p. 369 et seq. and p. 385 et seq.

The hydroxyimines of the formula VII can be obtained, for example, by the following synthetic routes [cf. J. Am. Pharm. Assoc. Vol. 35 (1946), p. 15]:

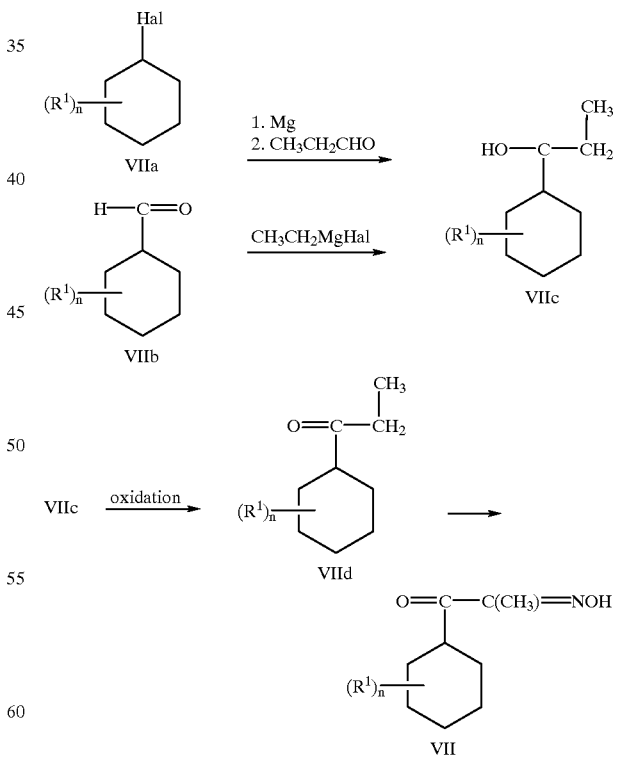

In the reaction scheme above, "Hal" is a halogen atom, in particular chlorine or bromine. The reaction of the compounds VIIa and VIIb, which follows a Grignard reaction, is carried out under generally customary conditions [cf.

Organikum (Organic Chemistry), VEB Deutscher Verlag der Wissenschaften, 15th Edition, p. 617 et seq., Berlin 1981].

Oxidation of the alcohol VIIc can be effected under generally customary conditions [cf. Houben-Weyl, Methoden der organischen Chemie (Methods in Organic Chemistry), Vol. VII/2a, 4th Edition, pp. 699–776, Georg Thieme Verlag, Stuttgart 1973]. Suitable oxidants are generally oxygen-transferring compounds such as, for example, hydrogen peroxide, chromium(VI) compounds, manganese compounds, nitrogen-oxygen compounds (for example nitric acid), dimethyl sulfoxide or compounds with positively induced halogen (for example hypohalites).

Conversion of the ketone VIId into an oxime is normally carried out in an inert organic solvent in the presence of an acid or base [cf. Houben-Weyl, Methoden der organischen Chemie (Methods in Organic Chemistry), Vol. X/4, 4th Edition, pp. 10–27 Georg Thieme Verlag, Stuttgart 1968].

The starting materials VIIa and VIIb are known and some are commercially available.

Alternatively, the compounds I may also be obtained by first reacting the benzyl derivative II with the carbonylhydroxyimino derivative VII to give a corresponding benzyloxyimine of the formula VIII, VIII subsequently being reacted with the hydroxylamine IXa or a salt thereof IXb to give I.

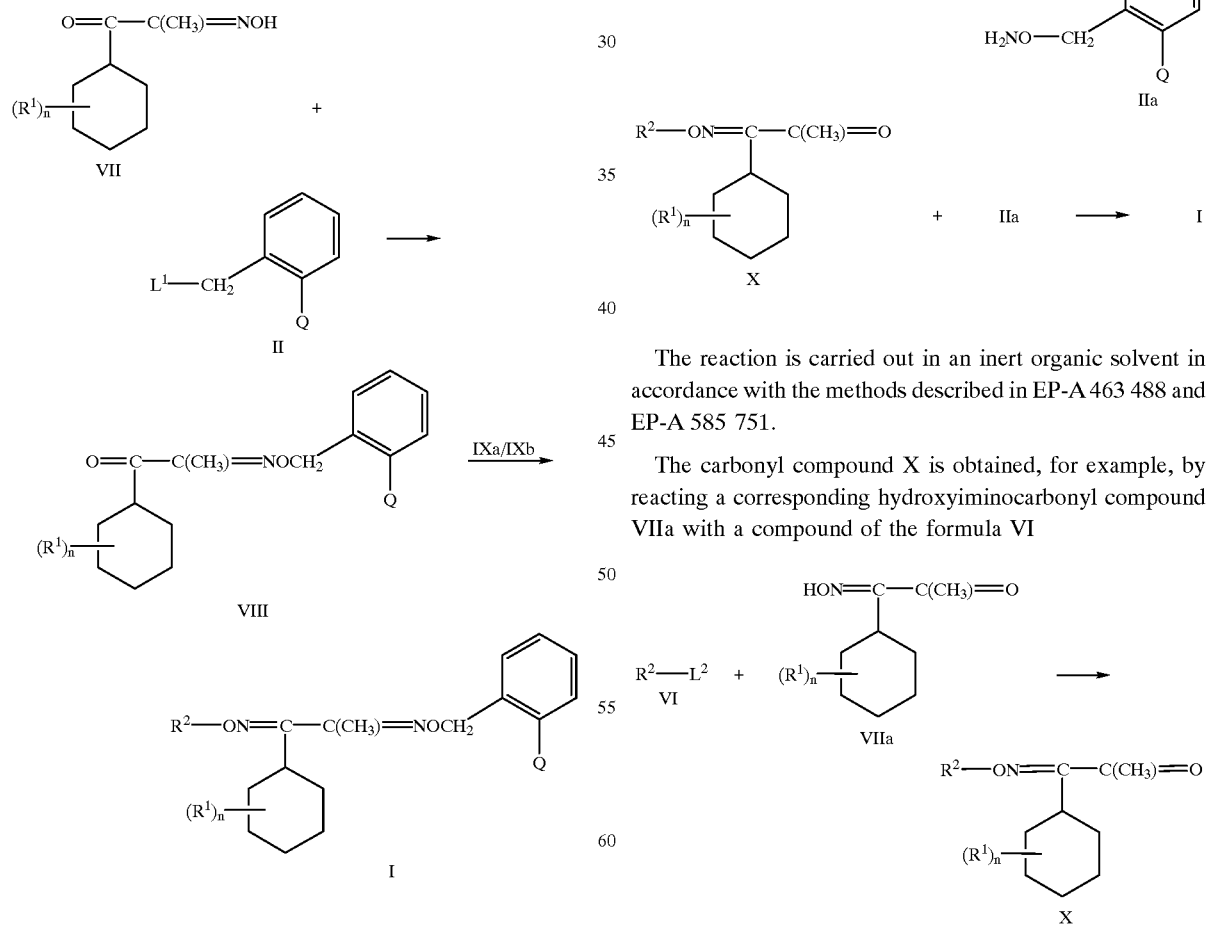

The reaction is carried out in an inert organic solvent in accordance with the methods described in Houben-Weyl, Methoden der organischen Chemie (Methods in Organic Chemistry), Georg Thieme Verlag Stuttgart 1980, 4th Edition, Vol. E 14b, p. 369 et seq., Vol. 10/1, p. 1189 et seq. and Vol. 10/4, p. 73 et seq. or EP-A 513 580.

A further possibility of preparing the compounds I is to react the benzyl derivative II with N-hydroxyphthalimide and subsequently subjecting the product to hydrazinolysis to give the benzylhydroxylamine IIa, which is reacted further with a carbonyl compound X.

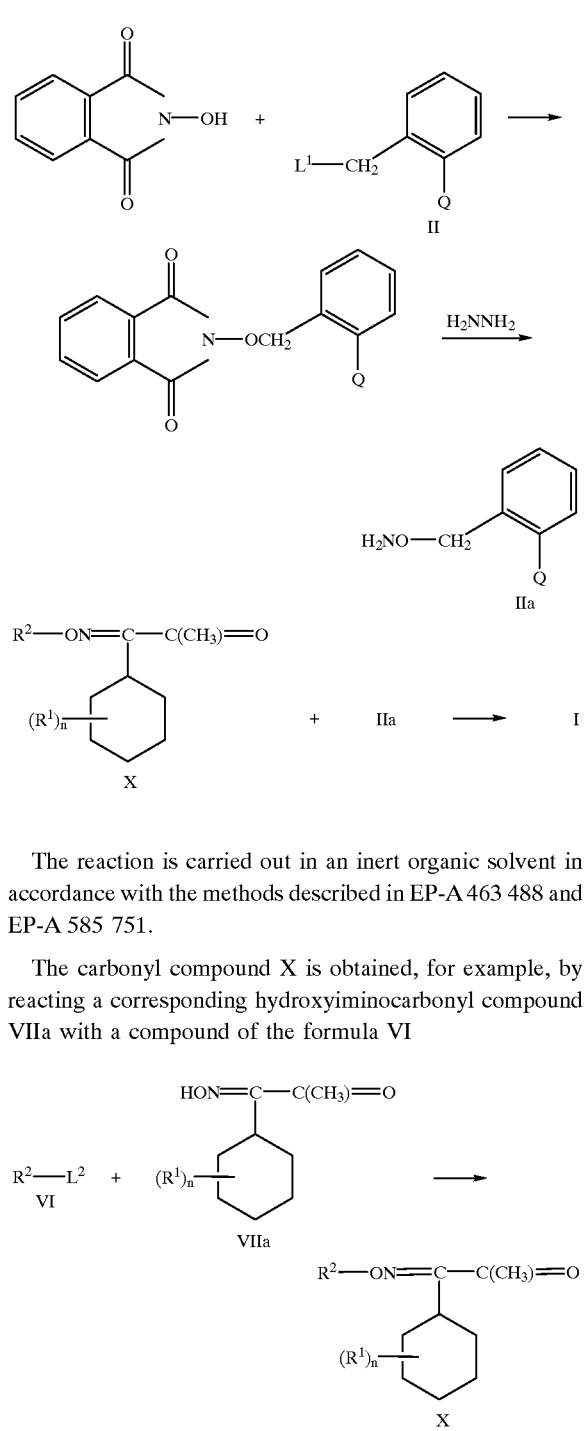

The reaction is carried out in an inert organic solvent in accordance with the methods described in EP-A 463 488 and EP-A 585 751.

The carbonyl compound X is obtained, for example, by reacting a corresponding hydroxyiminocarbonyl compound VIIa with a compound of the formula VI or by reacting a corresponding dicarbonyl compound XI with a hydroxylamine IXa or a salt thereof IXb

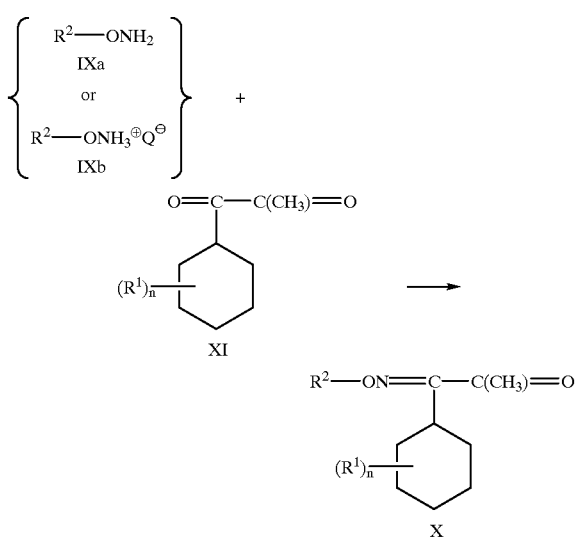

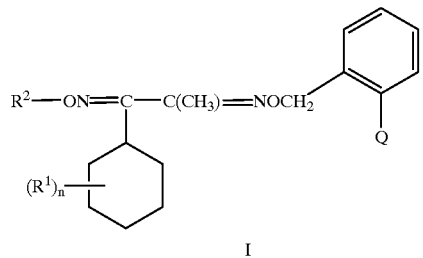

The reactions are carried out in an inert organic solvent in accordance with the methods described in EP-A 513 580, Houben-Weyl, 4th Edition, Vol. 10/4, p. 55 et seq., p 73 et seq., p. 180 et seq. and p. 217 et seq., Vol. E 14b, p. 307 et seq. and 369 et seq., Vol. E 5, p. 780 et seq.

The compounds of the formula VIIa or XI can be prepared by known methods [cf. J. Chem. Soc. (1955), 3094; Bull. Soc. Chim. Fr. (1969), 2894; Tetrahedron 40 (1984), 2035; J. Org. Chem. USSR (Engl. transl.) Vol. 2 (1966) p. 848; J. Org. Chem. Vol. 35 (1970) p. 3007; Tetrahedron Vol. 52 (1996) p. 14225; Synth. Commun. Vol. 22 (1992) p. 1049; Synthesis Vol. 6 (1986) p. 473; Angew. Chem. Vol. 98 (1986) p. 1134].

Similarly, the compounds I may also be obtained by first reacting the benzylhydroxylamine IIa with the hydroxyimino derivative VIIa to give the corresponding benzyloxyimino derivative of the formula V, V subsequently being reacted with a compound of the formula VI as described above to give I.

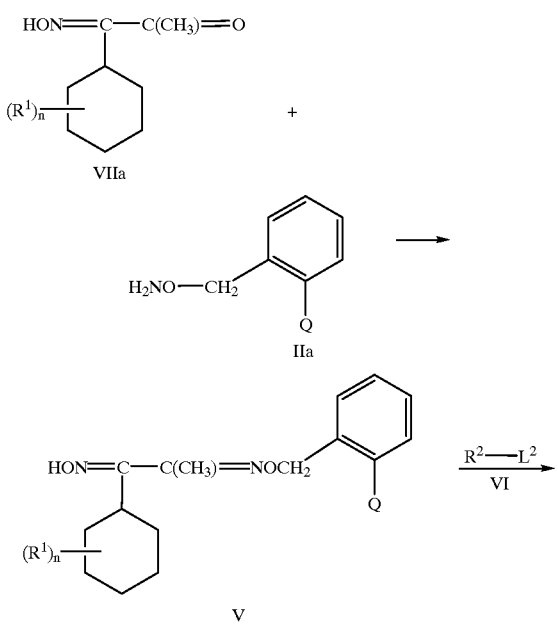

Similarly, the compounds I may also be prepared by first converting the benzylhydroxylamine IIa with the dicarbonyl derivative of the formula XI into the benzyloxyimino derivative of the formula VIII and subsequently reacting VIII with the hydroxylamine IXa or a salt thereof IXb as described above to give I.

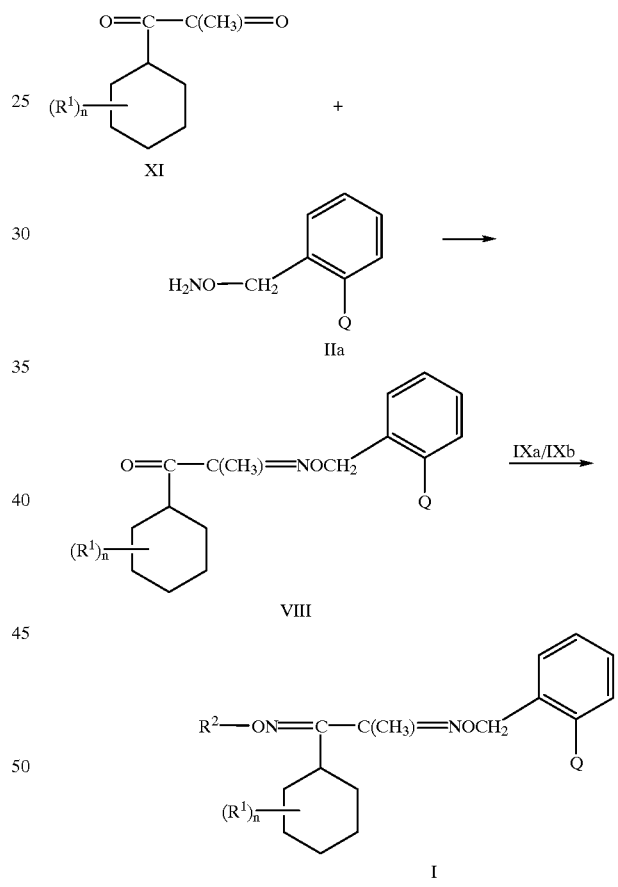

Moreover, the compounds I are also obtained by first converting a compound III with a lactone XII in accordance with the methods described in EP-A 493 711 to give the corresponding benzoic acid XIII and converting XIII via the corresponding halides into the cyanocarboxylic acids XIV, which are converted into the α-keto esters XV via a Pinner reaction (Angew. Chem. 94 (1982), 1) and, if appropriate, reacted further to give the a-ketoamides XVI (cf. EP-A 348 766, EP-A 280 185, EP-A 178 826, EP-A 253213, Houben-Weyl, 4th Edition, Vol. E5, p. 941 et seq.).

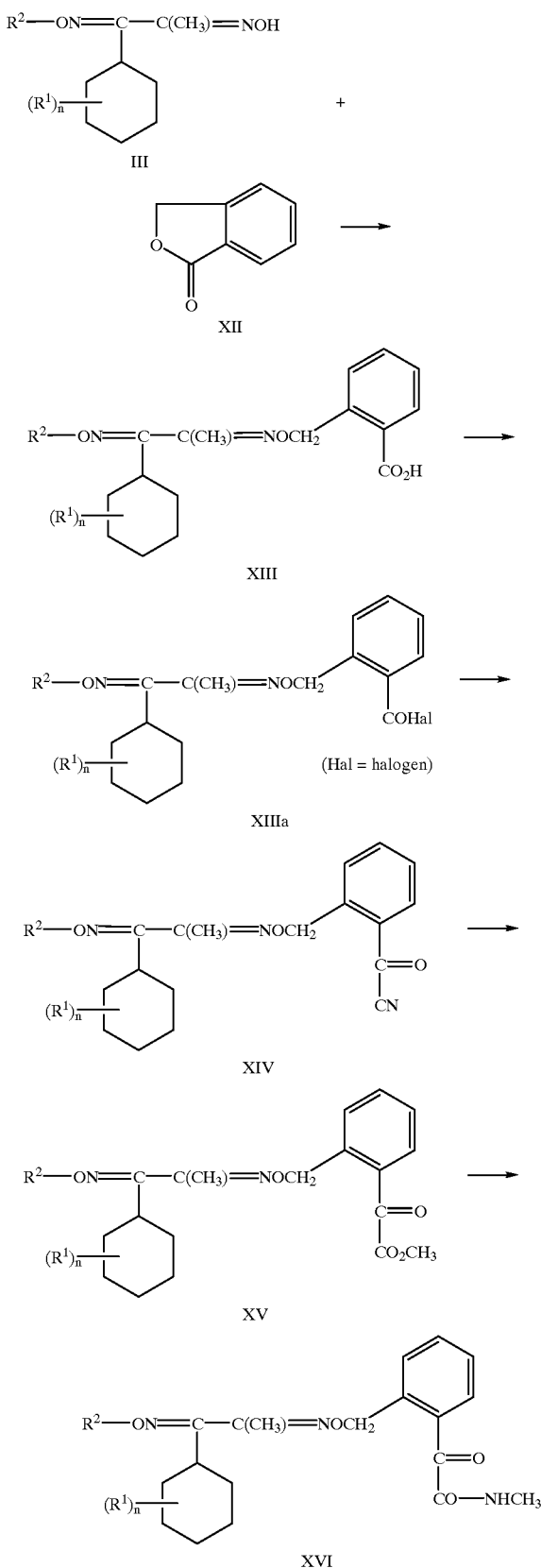

The α-ketoesters XV and the a-ketoamides XVI can be converted into the compounds I in accordance with customary processes (cf. EP-A 178 826, EP-A 513 580, EP-A 253 213, EP-A 398 692).

Those compounds I in which Q is C(=NOCH$_3$)CONHCH$_3$ may also be obtained by reacting the corresponding esters [Q=C(=NOCH$_3$)COOCH$_3$] with methylamine.

Those compounds II which are not already known (EP-A 513 580, EP-A 477 631, EP-A 463 488, EP-A 251 082, EP-A 400 417, EP-A 585 751) can be prepared by the methods described therein.

If individual compounds I are not accessible by the routes described above, they can be prepared by derivatizing other compounds I.

The reaction mixtures are worked up in the customary manner, for example by mixing with water, phase separation and, if appropriate, chromatographic purification of the crude products. In some cases, the intermediates and end products are obtained in the form of colorless or pale brown viscous oils which are purified or freed from volatile components under reduced pressure and at moderately elevated temperature. If the intermediates and end products are obtained as solids, they may also be purified by recrystallization or digestion.

Preparation of the compounds I may yield them, owing to their C=C and C=N double bonds, as E/Z isomer mixtures, and these may be separated into the individual compounds in the customary manner, for example by crystallization or chromatography.

If the synthesis yields isomer mixtures, however, separation is generally not absolutely necessary since some of the individual isomers may be converted into each other during processing for use, or upon use (for example with the action of light, acids or bases). Similar conversions may also take place after use, for example in the case of the treatment of plants in the treated plant or in the harmful fungi or animal pest to be controlled. As regards the C=C or C=N double bond in group Q, the E isomers of the compounds I are preferred regarding their activity (configuration based on the —OCH$_3$ or the —CH$_3$ group relative to the —COOCH$_3$ or —CONHCH$_3$ group).

As regards the —C(CH$_3$)=NOCH$_2$ double bond, the cis isomers of the compounds I are preferred regarding their activity (configuration based on the methyl group relative to the —OCH$_2$ group).

As regards the C=N—OR$^2$ double bond, the cis isomers of the compounds I are preferred regarding their activity (configuration based on the R$^2$O group relative to the cyclohexyl group).

As regards the variables, the especially preferred embodiments of the intermediates are those of the radicals (R$^1$)$_n$, R$^2$ and Q of the formula I.

Collective terms which generally represent the following groups are used in the definitions of the compounds I given at the outset:

Halogen: fluorine, chlorine, bromine and iodine;

Alkyl: straight-chain or branched alkyl groups having 1 to 4 carbon atoms such as methyl, ethyl, propyl, 1-methylethyl, butyl, 1-methylpropyl, 2-methylpropyl or 1,1-dimethylethyl;

Haloalkyl: straight-chain or branched alkyl groups having 1 to 4 carbon atoms, it being possible for some or all of the hydrogen atoms in these groups to be replaced by halogen atoms as mentioned above, for example $C_{1-C_2}$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 carbon atoms as mentioned above which are bonded to the skeleton via an oxygen atom (—O—), such as methyloxy, ethyloxy, propyloxy, 1-methylethyloxy, butyloxy, 1-methylpropyloxy, 2-methylpropyloxy or 1,1-dimethylethyloxy;

Haloalkoxy: straight-chain or branched alkyl groups having 1 to 4 carbon atoms, it being possible for some or all of the hydrogen atoms in these groups to be replaced by halogen atoms as mentioned above, and these groups being bonded to the skeleton via an oxygen atom;

Alkenyl: straight-chain or branched alkenyl groups having 3 to 6 carbon atoms and a double bond wherever desired, such as 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched alkynyl groups having 3 to 6 carbon atoms and a triple bond wherever desired, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

The term "partially or fully halogenated" is intended to express that some or all of the hydrogen atoms in groups characterized thus may be replaced by identical or different halogen atoms as mentioned above.

Especially preferred with a view to the intended use of the bisoxime ether derivatives of the formula I are the following meanings of the substituents, in each case alone or in combination:

Particularly preferred compounds I are those in which $R^1$ is in the trans-position relative to the linkage of the cyclohexyl ring.

Especially preferred compounds I are those in which $R^1$ is $C_{1-C_1}$-alkyl.

Moreover, particularly preferred compounds I are those in which $R^1$ is $C_1-C_4$-alkoxy.

Furthermore, preferred compounds I are those in which $R^1$ is halogen.

Equally, particularly preferred compounds I are those in which the index n is 1.

Also, particularly preferred compounds I are those in which $R^2$ is $C_1-C_3$-alkyl, $C_3-C_4$-alkenyl or $C_3-C_4$-alkynyl.

Other especially preferred compounds I are those in which $R^2$ is methyl or propargyl.

Moreover, particularly preferred are the compounds I.1

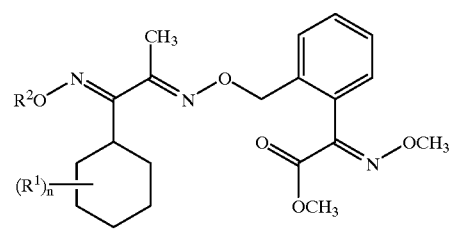

I.1

Equally, especially preferred are the compounds I.2.

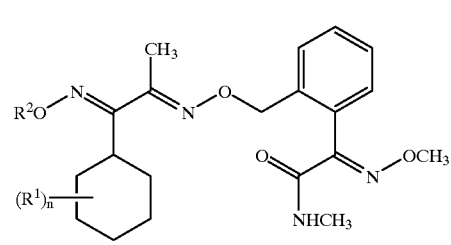

I.2

Especially preferred are the compounds I.3.

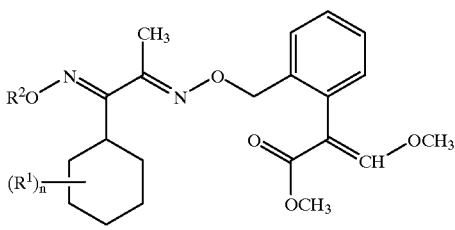

I.3

Furthermore, especially preferred are the compounds I.4.

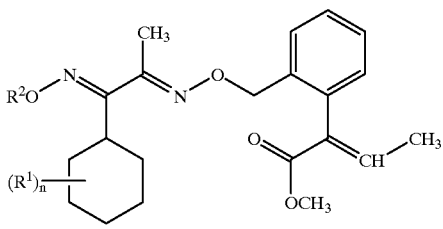

I.4

Particularly preferred with a view to their use are the compounds I which are compiled in the tables which follow. In these tables, the groups mentioned for a substituent are also on their own, independently of the combination in which they are mentioned, a particularly preferred embodiment of the substituent in question.

Table 1
Compounds of the general formula I.1 in which $R^2$ is methyl and $(R^1)_n$ for each compound corresponds to one line of Table A Table 2
Compounds of the general formula I.2, in which $R^2$ is methyl and $(R^1)_n$ for each compound corresponds to one line of Table A Table 3
Compounds of the general formula I.3, in which $R^2$ is methyl and
$(R^1)_n$ for each compound corresponds to one line of Table A Table 4
Compounds of the general formula I.4, in which $R^2$ is methyl and $(R^1)_n$ for each compound corresponds to one line of Table A Table 5
Compounds of the general formula I.1, in which $R^2$ is ethyl and $(R^1)_n$ for each compound corresponds to one line of Table A Table 6
Compounds of the general formula I.2, in which $R^2$ is ethyl and $(R^1)_n$ for each compound corresponds to one line of Table A Table 7
Compounds of the general formula I.3 in which $R^2$ is ethyl and $(R^1)_n$ for each compound corresponds to one line of Table A Table 8
Compounds of the general formula I.4 in which $R^2$ is ethyl and $(R^1)_n$ for each compound corresponds to one line of Table A Table 9
Compounds of the general formula I.1 in which $R^2$ is n-propyl and $(R^1)_n$ for each compound corresponds to one line of Table A Table 10
Compounds of the general formula I.2 in which $R^2$ is n-propyl and $(R^1)_n$ for each compound corresponds to one line of Table A Table 11
Compounds of the general formula I.3 in which $R^2$ is n-propyl and $(R^1)_n$ for each compound corresponds to one line of Table A Table 12
Compounds of the general formula I.4 in which $R^2$ is n-propyl and $(R^1)_n$ for each compound corresponds to one line of Table A Table 13
Compounds of the general formula I.1 in which $R^2$ is iso-propyl and $(R^1)_n$ for each compound corresponds to one line of Table A Table 14
Compounds of the general formula I.2 in which $R^2$ is iso-propyl and $(R^1)_n$ for each compound corresponds to one line of Table A Table 15
Compounds of the general formula I.3 in which $R^2$ is iso-propyl and $(R^1)_n$ for each compound corresponds to one line of Table A Table 16
Compounds of the general formula I.4 in which $R^2$ is iso-propyl and $(R^1)_n$ for each compound corresponds to one line of Table A Table 17
Compounds of the general formula I.1 in which $R^2$ is difluoromethyl and $(R^1)_n$ for each compound corresponds to one line of Table A Table 18
Compounds of the general formula I.2 in which $R^2$ is difluoromethyl and $(R^1)_n$ for each compound corresponds to one line of Table A Table 19
Compounds of the general formula I.3 in which $R^2$ is difluoromethyl and $(R^1)_n$ for each compound corresponds to one line of Table A Table 20
Compounds of the general formula I.4 in which $R^2$ is difluoromethyl and $(R^1)_n$ for each compound corresponds to one line of Table A Table 21
Compounds of the general formula I.1 in which $R^2$ is 2,2,2-trifluoro-1-ethyl and $(R^1)_n$ for each compound corresponds to one line of Table A Table 22
Compounds of the general formula I.2 in which $R^2$ is 2,2,2-trifluoro-1-ethyl and $(R^1)_n$ for each compound corresponds to one line of Table A Table 23
Compounds of the general formula I.3 in which $R^2$ is 2,2,2-trifluoro-1-ethyl and $(R^1)_n$ for each compound corresponds to one line of Table A Table 24
Compounds of the general formula I.4 in which $R^2$ is 2,2,2-trifluoro-1-ethyl and $(R^1)_n$ for each compound corresponds to one line of Table A Table 25
Compounds of the general formula I.1 in which $R^2$ is propargyl and $(R^1)_n$ for each compound corresponds to one line of Table A Table 26
Compounds of the general formula I.2 in which $R^2$ is propargyl and $(R^1)_n$ for each compound corresponds to one line of Table A Table 27
Compounds of the general formula I.3 in which $R^2$ is propargyl and $(R^1)_n$ for each compound corresponds to one line of Table A Table 28
Compounds of the general formula I.4 in which $R^2$ is propargyl and $(R^1)_n$ for each compound corresponds to one line of Table A Table 29
Compounds of the general formula I.1 in which $R^2$ is 3-chloropropargyl and $(R^1)_n$ for each compound corresponds to one line of Table A Table 30
Compounds of the general formula I.2 in which $R^2$ is 3-chloropropargyl and $(R^1)_n$ for each compound corresponds to one line of Table A Table 31
Compounds of the general formula I.3 in which $R^2$ is 3-chloropropargyl and $(R^1)_n$ for each compound corresponds to one line of Table A Table 32
Compounds of the general formula I.4 in which $R^2$ is 3-chloropropargyl and $(R^1)_n$ for each compound corresponds to one line of Table A Table 33
Compounds of the general formula I.1 in which $R^2$ is allyl and $(R^1)_n$ for each compound corresponds to one line of Table A Table 34
Compounds of the general formula I.2 in which $R^2$ is allyl and $(R^1)_n$ for each compound corresponds to one line of Table A Table 35
Compounds of the general formula I.3 in which $R^2$ is allyl and $(R^1)_n$ for each compound corresponds to one line of Table A Table 36
Compounds of the general formula I.4 in which $R^2$ is allyl and $(R^1)_n$ for each compound corresponds to one line of Table A Table 37
Compounds of the general formula I.1 in which $R^2$ is 2-chloroallyl and $(R^1)_n$ for each compound corresponds to one line of Table A Table 38
Compounds of the general formula I.2 in which $R^2$ is 2-chloroallyl and $(R^1)_n$ for each compound corresponds to one line of Table A Table 39
Compounds of the general formula I.3 in which $R^2$ is 2-chloroallyl and $(R^1)_n$ for each compound corresponds to one line of Table A Table 40
Compounds of the general formula I.4 in which $R^2$ is 2-chloroallyl and $(R^1)_n$ for each compound corresponds to one line of Table A Table 41
Compounds of the general formula I.1 in which $R^2$ is E-3-chloroallyl and $(R^1)_n$ for each compound corresponds to one line of Table A Table 42
Compounds of the general formula I.2 in which $R^2$ is E-3-chloroallyl and $(R^1)_n$ for each compound corresponds to one line of Table A Table 43
Compounds of the general formula I.3 in which $R^2$ is E-3-chloroallyl and $(R^1)_n$ for each compound corresponds to one line of Table A Table 44
Compounds of the general formula I.4 in which $R^2$ is E-3-chloroallyl and $(R^1)_n$ for each compound corresponds to one line of Table A Table 45
Compounds of the general formula I.1 in which $R^2$ is Z-3-chloroallyl and $(R^1)_n$ for each compound corresponds to one line of Table A Table 46
Compounds of the general formula I.2 in which $R^2$ is Z-3-chloroallyl and $(R^1)_n$ for each compound corresponds to one line of Table A Table 47
Compounds of the general formula I.3 in which $R^2$ is Z-3-chloroallyl and $(R^1)_n$ for each compound corresponds to one line of Table A Table 48
Compounds of the general formula I.4 in which $R^2$ is Z-3-chloroallyl and $(R^1)_n$ for each compound corresponds to one line of Table A Table 49
Compounds of the general formula I.1 in which $R^2$ is 3,3-dichloroallyl and $(R^1)_n$ for each compound corresponds to one line of Table A Table 50
Compounds of the general formula I.2 in which $R^2$ is 3,3-dichloroallyl and $(R^1)_n$ for each compound corresponds to one line of Table A Table 51
Compounds of the general formula I.3 in which $R^2$ is 3,3-dichloroallyl and $(R^1)_n$ for each compound corresponds to one line of Table A Table 52
Compounds of the general formula I.4 in which $R^2$ is 3,3-dichloroallyl and $(R^1)_n$ for each compound corresponds to one line of Table A

TABLE A

| No. | $(R^1)_n$ |
|---|---|
| A-1 | 1-Fluoro |
| A-2 | 2-Fluoro |
| A-3 | 3-Fluoro |
| A-4 | 4-Fluoro |
| A-5 | 1-Chloro |
| A-6 | 2-Chloro |
| A-7 | 3-Chloro |
| A-8 | 4-Chloro |
| A-9 | 1-Bromo |
| A-10 | 2-Bromo |
| A-11 | 3-Bromo |
| A-12 | 4-Bromo |
| A-13 | 1-Methyl |
| A-14 | 2-Methyl |
| A-15 | 3-Methyl |
| A-16 | 4-Methyl |
| A-17 | 1-Ethyl |
| A-18 | 2-Ethyl |
| A-19 | 3-Ethyl |
| A-20 | 4-Ethyl |
| A-21 | 1-n-Propyl |
| A-22 | 3-n-Propyl |
| A-23 | 4-n-Propyl |
| A-24 | 1-iso-Propyl |
| A-25 | 3-iso-Propyl |
| A-26 | 4-iso-Propyl |
| A-27 | 3-n-Butyl |
| A-28 | 4-n-Butyl |
| A-29 | 3-(2-Butyl) |
| A-30 | 4-(2-Butyl) |
| A-31 | 3-(2-Methyl-propyl) |
| A-32 | 4-(2-Methyl-propyl) |

TABLE A-continued

| No. | $(R^1)_n$ |
|---|---|
| A-33 | 3-tert-Butyl |
| A-34 | 4-tert-Butyl |
| A-35 | 2-Trifluoromethyl |
| A-36 | 3-Trifluoromethyl |
| A-37 | 4-Trifluoromethyl |
| A-38 | 1-Methoxy |
| A-39 | 2-Methoxy |
| A-40 | 3-Methoxy |
| A-41 | 4-Methoxy |
| A-42 | 3-Ethoxy |
| A-43 | 4-Ethoxy |
| A-44 | 3-n-Propoxy |
| A-45 | 4-n-Propoxy |
| A-46 | 3-iso-Propoxy |
| A-47 | 4-iso-Propoxy |
| A-48 | 2,4-Dichloro |
| A-49 | 2-Trifluoromethoxy |
| A-50 | 3-Trifluoromethoxy |
| A-51 | 4-Trifluoromethoxy |
| A-52 | 1,2-Dichloro |
| A-53 | 1,3-Dichloro |
| A-54 | 1,4-Dichloro |
| A-55 | 3,4-Dichloro |
| A-56 | 3,5-Dichloro |
| A-57 | 2,4-Difluoro |
| A-58 | 3,4-Difluoro |
| A-59 | 3,5-Difluoro |
| A-60 | 1,2-Dimethyl |
| A-61 | 1,3-Dimethyl |
| A-62 | 1,4-Dimethyl |
| A-63 | 2,4-Dimethyl |
| A-64 | 3,4-Dimethyl |
| A-65 | 3,5-Dimethyl |
| A-66 | 3,4-Diethyl |
| A-67 | 3,5-Diethyl |
| A-68 | 1-Chloro, 2-Methyl |
| A-69 | 1-Chloro, 3-Methyl |
| A-70 | 1-Chloro, 4-Methyl |
| A-71 | 2-Chloro, 4-Methyl |
| A-72 | 3-Chloro, 1-Methyl |
| A-73 | 3-Chloro, 4-Methyl |
| A-74 | 3-Chloro, 5-Methyl |
| A-75 | 4-Chloro, 1-Methyl |
| A-76 | 4-Chloro, 2-Methyl |
| A-77 | 4-Chloro, 3-Methyl |

The compounds I are suitable as fungicides. They are distinguished by an outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,

*Botrytis cinerea* (gray mold) on strawberries, vegetables, ornamentals and grapevines,

*Cercospora arachidicola* on peanuts, i Erysiphe cichoracearumand *Sphaerotheca fuliginea* on cucurbits,

*Erysiphe graminis* (powdery mildew) on cereals,

Fusarium and Verticillium species on various plants,

Helminthosporium species on cereals,

Mycosphaerella species on bananas and peanuts,

*Phytophthora infestans* on potatoes and tomatoes,

*Plasmopara viticola* on grapevines,

*Podosphaera leucotricha* on apples,

*Pseudocercosporella herpotrichoides* on wheat and barley,

Pseudocercosporella species on hops and cucumbers,

Puccinia species on cereals,

*Pyricularia oryzae* on rice,

Rhizoctonia species on cotton, rice and turf,

*Septoria nodorum* on wheat,

*Uncinula necator* on grapevines,

Ustilago species on cereals and sugar cane, and

Venturia species (scab) on apples and pears.

Moreover, the compounds I are suitable for controlling harmful fungi such as *Paecilomyces variotii* in the protection of materials (eg. wood, paper, paint dispersions, fibers and fabrics) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90% by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

Moreover, the compounds of the formula I are suitable for efficiently controlling animal pests from the classes of the insects, arachnids and nematodes. They can be employed in crop protection and in the hygiene, stored-product and veterinary sector for controlling animal pests. In particular, they are suitable for controlling the following animal pests:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, orgyia pseudotsugata,*

*Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus* [sic] *sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria,* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina* [sic], *Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* thrips (Thysanoptera), eg. *Frankliniella fusca, Frankliniella occidentalis, Frankliniella tritici, Scirtothrips citri, Thrips oryzae, Thrips palmi* and *Thrips tabaci,* hymenopterans (Hymenoptera), eg. *Athalia rosae, Atta cephalotes, Atta sexdens, Atta texana, Hoplocampa minuta, Hoplocampa testudinea, Monomorium pharaonis, Solenopsis geminata* and *Solenopsis invicta,* heteropterans (Heteroptera), eg. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterans (Homoptera), eg. *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* termites (Isoptera), eg. *Calotermes flavicollis, Leucotermes flavipes, Reticulitermes lucifugus* and *Termes natalensis,* orthopterans (Orthoptera), eg. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,*

Arachnoidea, such as arachnids (Acarina), eg. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root knot nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The rate of application of active ingredient for controlling animal pests is from 0.1 to 2.0, preferably 0.2 to 1.0, kg/ha under field conditions.

The compounds I can be converted into the customary formulations, eg. solutions, emulsions, suspensions, dusts, powders, pastes and granules. The use form depends on the particular purpose; it is intended to ensure in each case a fine and uniform distribution of the compound according to the invention.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg.

mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silica gel, silicas, silica gels [sic], silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient)

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Various types of oils, herbicides, fungicides, other pesticides, or bactericides may be added to the active ingredients, if appropriate just immediately prior to use (tank mix). These agents can be admixed with the compositions according to the invention in a weight ratio of 1:10 to 10:1.

In the use form as fungicides, the compositions according to the invention can also be present together with other active ingredients, eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carboxcyclohexylamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurins such as methyl E-methoxyimino-[α-(o-tolyloxy)-o-tolyl]acetate, methyl E-2-{2-[6-(2-cyanophenoxy)pyrimidin-4-yloxy]-phenyl}-3-methoxyacrylate, N-methyl-E-methoxy-imino-[α-(2-phenoxyphenyl)]acetamide, N-methyl-E-methoxyimino-[α-(2,5-dimethylphenoxy)-o-tolyl]acetamide;

anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline;

phenylpyrroles such as 4-(2,2-difluoro-1,3-benzodioxol-4-yl)pyrrole-3-carbonitrile;

cinnamamides such as 3-(4-chlorophenyl)-3-(3,4-dimethoxyphenyl)acryloylmorpholide;

and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-amino butyrolactone, DL-N-(2,6-dimethylphenyl)-N-(phenylacetyl) alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-methylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

SYNTHESIS EXAMPLES

With due modification of the starting compounds, the protocols shown in the synthesis examples below were used for obtaining further compounds I. The resulting compounds, together with physical data, are listed in the Tables which follow.

Example 1

Preparation of 1-(4-methylcyclohexyl)propan-1-ol 180 ml (0.36 mol) of a 2 M ethylmagnesium chloride solution in tetrahydrofuran (THF) was first treated with a solution of 37.8 g (0.3 mol) of 4-methylcyclohexanecarbaldehyde (cis/trans) in 70 ml of THF and then stirred under protective gas atmosphere for approximately 16 hours at 20–25° C. After addition of 250 ml of 15% by weight ammonium chloride solution, the mixture was acidified with semiconcentrated hydrochloric acid and then extracted with methyl tert-butyl ether (MTBE). Washing of the combined organic phases with water and drying gave 44 g of 1-(4-methylcyclohexyl)propan-1-ol as a colorless oil. According to $^1$H NMR analysis, the ratio between the cis and trans isomers in the mixture amounted to approximately 35:65.

IR (film): 3371, 2946, 2921, 2867, 1455, 1448, 1376, 1067, 1043, 946 cm$^{-1}$.

Example 2

Preparation of 4-methylcyclohexyl ethyl ketone

A solution of 44 g (0.3 mol) of the alcohol of Example 1 in 200 ml of methyl tert-butyl ether (MTBE) was treated at not more than 20° C. with a solution of 42.9 g of Na$_2$Cr$_2$O$_7$*2H$_2$O in 210 ml of water and 35 ml of concentrated H$_2$SO$_4$. After the mixture had been stirred for approximately 16 hours at 20–25° C., the phases were separated and the aqueous phase was extracted with MTBE. After washing with water and drying, the combined organic phases [lacuna] distilled. The distillation gave 34.3 g of 4-methylcyclohexyl ethyl ketone as a colorless oil of b.p.$_{50}$ of 114–116° C. According to $^{13}$C NMR analysis, the ratio between the cis and trans isomers in the mixture amounted to approximately 30:70.

IR (film): 2926, 2868, 1709, 1457, 1413, 1377, 1348, 1148, 1109, 952 cm$^{-1}$.

Example 3

Preparation of (E)-1-(4-methylcyclohexyl)-1-oxopropane 2-oxime

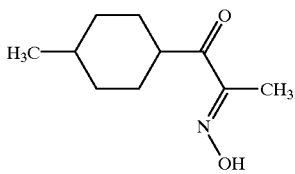

A solution of 34 g (0.22 mol) of the ketone of Example 2 in 195 ml of toluene was treated at −20° C. with 73 ml of saturated etheric HCl solution and then with a solution of 26 g (0.25 mol) of n-butyl nitrite in 65 ml of diethyl ether. After the reaction mixture had been stirred for two hours at 0° C. and for approx. 16 hours at 20–25° C., it was poured into ice-water and extracted with methyl tert-butyl ether (MTBE). The organic phase was extracted with a 5% strength sodium hydroxide solution, and the alkaline aqueous phase was acidifed with dilute hydrochloric acid and then extracted with MTBE. The organic phase was washed and dried. Removal of the solvent by distillation and recrystallization from n-hexane gave 19.2 g of the title compound as beige crystals. According to $^1$H NMR analysis, the compound was present as the trans isomer.

IR (KBr): 3320, 2951, 2945, 2935, 2919, 1663, 1449, 1368, 1008 cm$^{-1}$.

Example 4

Preparation of (E,E)-1-(4-methylcyclohexyl)-2-hydroxyimino-1-propane O-methyloxime

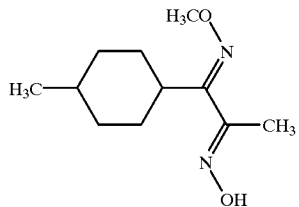

A mixture of 18.3 g (0.1 mol) of the oxime of Example 3, 24 g of pyridine and 12.5 g (0.15 mol) of O-methylhydroxylamine hydrochloride in 200 ml of methanol was first stirred for approx. 16 hours at 20–25° C. and then poured into ice-water, acidified with dilute hydrochloric acid and extracted with methyl tert-butyl ether (MTBE). The organic phase was washed with water, dried and then freed from solvent. The solution of the residue in 300 ml of toluene was treated with 4.1 g of AlCl$_3$ and stirred for 8 hours at 60° C. and then for a further 16 hours at 20–25° C. The solvent was distilled off and the residue was taken up in methylene chloride. The organic phase was washed with 5% strength hydrochloric acid and water, dried and then freed from solvent. After silica gel chromatography (cyclohexane/MTBE 20:1), 9.7 g of the title compound were obtained as an ochre oil. According to $^1$H NMR analysis, the compound was present as the trans isomer.

IR (film): 2948, 2926, 2868, 2845, 1451, 1057, 1006, 976, 909, 865 cm$^{-1}$.

Example 5

Preparation of I-1

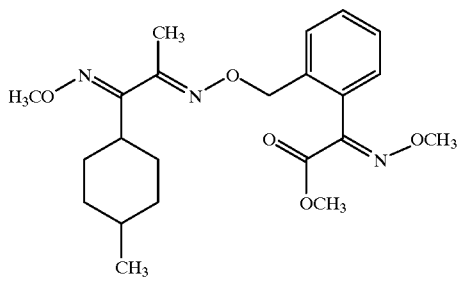

A solution of 2.12 g (10 mmol) of the bisoxime of Example 4 and 2.86 g (10 mmol) of methyl 2-bromomethylphenylglyoxylate trans-o-methyloxime [EP-A 254 426] in 30 ml of N,N-dimethylformamide (DMF)

was treated with 1.98 g of 30% strength methanolic sodium methoxide solution and stirred for approx. 16 hours at 20–25° C. The mixture was poured into ice-water and then extracted with methyl tert-butyl ether (MTBE). The organic phase was washed with water and dried and then freed from solvent. After chromatography on silica gel (cyclohexane/MTBE 10:1), 3.44 g of the title compound were obtained as colorless crystals. According to $^1$H NMR analysis, the compound was present as the trans isomer.

Example 6

Preparation of I-2

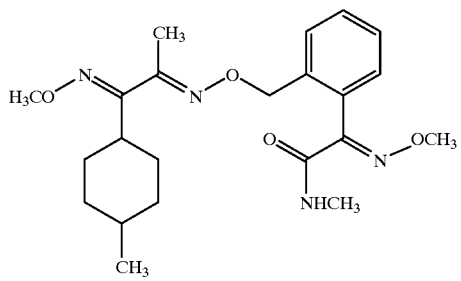

A solution of 2.3 g (5.5 mmol) of compound I-1 of Example 5 in 30 ml of tetrahydrofuran (THF) was treated with 4.3 g of 40% strength aqueous methylamine solution and stirred for three hours at 45° C. and for approx. 16 hours at 20–25° C. After the solvent had been distilled off, the residue was taken up in methyl tert-butyl ether (MTBE), and the solution was washed with water and dried. After the solvent had been distilled off, 2.1 g of the title compound were obtained as colorless crystals. According to $^1$H NMR analysis, the compound was present as the trans isomer.

TABLE I

| No. | Formula | $(R^1)_n$ | $R^2$ | Physical data [m.p.: ° C.; IR: cm$^{-1}$ $^1$H-NMR: ppm] |
|---|---|---|---|---|
| I-1 | I.1 | 4-methyl | methyl | 67–69; 1736, 1220, 1077, 1058, 1021, 1009, 992, 905, 865, 778 |
| I-2 | I.2 | 4-methyl | methyl | 107–109; 3370, 1659, 1530, 1059, 1051, 1043, 1014, 996, 906, 755 |
| I-3 | I.3 | 4-methyl | methyl | 2947, 2926, 1711, 1635, 1256, 1130, 1111, 1055, 1013, 908 |
| I-4 | I.4 | 4-methyl | methyl | 2948, 2929, 2868, 1719, 1450, 1435, 1252, 1049, 1013, 907 |
| I-5 | I.4 | 4-methyl | propargyl | 1718, 1450, 1435, 1252, 1207, 1038 |
| I-6 | I.3 | 4-methyl | propargyl | 1710, 1634, 1255, 1129, 1111, 1043 |
| I-7 | I.3 | 4-methoxy | methyl | 1711, 1635, 1256, 1130, 1103, 1056 |
| I-8 | I.4 | 4-methoxy | methyl | 1719, 1253, 1102, 1051, 1006 |
| I-9 | I.1 | 4-methoxy | methyl | 1737, 1305, 1101, 1071, 1043, 1013 |
| I-10 | I.2 | 4-methoxy | methyl | 1660, 1530, 1105, 1097, 1060, 1043 |
| I-11 | I.1 | 2-methyl | methyl | 1730, 1219, 1070, 1020, 958, 886 |
| I-12 | I.4 | 2-methyl | methyl | 5.0(2H); 3.85(3H); 3.7(3H); 2.0(3H) |

TABLE I-continued

| No. | Formula | $(R^1)_n$ | $R^2$ | Physical data [m.p.: ° C.; IR: cm$^{-1}$ $^1$H-NMR: ppm] |
|---|---|---|---|---|
| I-13 | I.3 | 2-methyl | methyl | 1712, 1636, 1256, 1129, 1055 |
| I-14 | I.2 | 2-methyl | methyl | 1742, 1052, 957, 686 |

Examples for the Action Against Harmful Fungi

The fungicidal action of compounds of the general formula I was demonstrated by the following experiments:

The active ingredients, separately or together, were formulated as a 10% emulsion in a mixture of 70% by weight of cyclohexane, 20% by weight of Nekanil® LN (Lutensol® AP6, wetter having emulsifying and dispersant action, based on ethoxylated alkylphenols) and 10% by weight of Wettol® EM (non-ionic emulsifier based on ethoxylated castor oil) and diluted with water to give the desired concentration.

Compounds A, B, C and D, which are known from WO-A 97/05103 as Numbers A.2 of Tables No. 41, 42, 43 and 44, acted as comparison active ingredients:

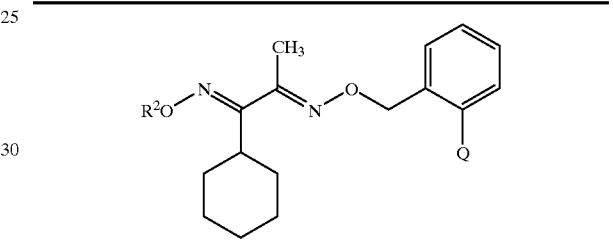

| No. | Disclosed in WO-A 97/05103 | $R^2$ | Q |
|---|---|---|---|
| A | Tab. 41, No. A.2 | methyl | C(=CHOCH$_3$)COOCH$_3$ |
| B | Tab. 42, No. A.2 | methyl | C(=CHCH$_3$)COOCH$_3$ |
| C | Tab. 43, No. A.2 | methyl | C(=NOCH$_3$)COOCH$_3$ |
| D | Tab. 44, No. A.2 | methyl | C(=NOCH$_3$)CONHCH$_3$ |

Example 1

Activity Against *Botrytis cinerea* on capsicum leaves

Capsicum seedlings cv. "Neusiedler Ideal Elite" were allowed to fully develop 4 to 5 leaves and then sprayed to runoff point with an aqueous preparation of active ingredient which had been made up from a stock solution of 10% active ingredient, 63% cyclohexanone and 27% emulsifier. Next day, the treated plants were inoculated with a spore suspension of *Botrytis cinerea* which contained 1.7×10$^6$ spores/ml in a 2% strength aqueous Biomalz solution. The test plants were subsequently placed into a controlled-environment cabinet at 22 to 24° C. and high atmospheric humidity. After 5 days, the extent of fungal infection on the leaves was determined visually in %.

In this test, the plants which had been treated with 250 ppm of active ingredients I-1, I-2, I-3 or I-4 showed a disease level of 0 to 25%, while the plants which had been treated with 250 ppm of the comparison active ingredients A, B, C and D, respectively, showed a disease level of 60 to 90% and the untreated plants also of 90%.

Example 2

Curative Activity Against *Puccinia recondita* on Wheat (Leaf Rust on Wheat)

Leaves of wheat seedling cv. "Kanzler" grown in pots were dusted with leaf rust spores (*Puccinia recondita*). The pots were then placed for 24 hours into a chamber with high atmospheric humidity (90 to 95%) and 20 to 22° C. During this time, the spores germinated and the germ tubes penetrated the leaf tissue. Next day, the infected plants were sprayed to runoff with an aqueous active ingredient preparation made with a stock solution consisting of 10% of active ingredient, 63% of cyclohexanone and 27% of emulsifier. After the spray coating had dried on, the test plants were grown in the greenhouse for 7 days at temperatures between 20 and 22° C. and a relative atmospheric humidity of 65 to 70%. The extent of rust development on the leaves was then determined.

In this experiment, a maximum disease level of 5% was shown by the plants treated with 1 ppm of the active ingredients I-2, I-3, I-7 and I-10, while the disease level of the untreated plants and of those which had been treated with 1 ppm of the comparative active ingredients A or D was 90%.

Example 3

Activity Against *Plasmopara viticola*

Leaves of grapes cv. "Müller-Thurgau!" in pots were sprayed to runoff with aqueous active ingredient preparations made with a stock solution of 10% active ingredient, 63% cyclohexanone and 27% of emulsifier. In order to be able to assess the long-term action of the substances, the spray coating was allowed to dry off and the plants were then placed in the greenhouse for 7 days. Only then were the leaves inoculated with an aqueous zoospore suspension of *Plasmopara viticola*. Then, the vines were first placed for 48 hours into a water-vapor-saturated chamber at 24° C. and then for 5 days in the greenhouse at temperatures between 20 and 30° C. After this time, the plants were returned to a humid chamber for 16 hours to accelerate sporangiophore eruption for 16 hours. The extent of the disease development on the undersides of the leaves was then determined visually.

In this experiment, a maximum disease level of 3% was shown by the plants which had been treated with 16 ppm of the active ingredients I-2 and I-10, while the disease level of the plants which had been treated with 16 ppm of the comparative active ingredient D was 60% and of the untreated plants 85%.

Examples for the Action Against Animal Pests

The action of the compounds of the formula I against animal pests was demonstrated by the following experiments:

The active ingredients were formulated
a. as a 0.1% strength solution in acetone or
b. as a 10% emulsion in a mixture of 70% by weight of cyclohexanone, 20% by weight of Nekanil® LN (Lutensol® AP6, wetter having emulsifying and dispersant action, based on ethoxylated alkylphenols) and 10% by weight of Wettol® EM (non-ionic emulsifier based on ethoxylated castor oil)
and diluted to give the desired concentration, using acetone in the case of a. and water in the case of b.

After the tests had been concluded, the lowest concentration was determined for each case at which the compounds still showed an inhibition or mortality of 80 to 100% in comparison to untreated control (limit or minimal concentration).

In these experiments too, compounds A, B, C and D, which are known from WO-A 97/05103 as Numbers A.2 of Tables No. 41, 42, 43 and 44, acted as comparison active ingredients.

Example 1

Action Against *Aphis fabae* (Black Louse [sic]), Contact Action

Severely infested dwarf beans (*Vicia faba*) in the four-leaf stage were treated with aqueous formulations of active ingredient. The mortality rate was determined after 24 hours.

In this experiment, the active ingredients I-1 and I-4 showed limit concentrations of 80 to 100 ppm, while the comparison active ingredients A and C showed limit concentrations of 100 ppm.

Example 2

Action Against *Prodenia litura* (Egyptian Cotton Leafworm), Contact and Stomach Action Filter disks (Ø 9 cm) which had been treated with aqueous formulations of active ingredient were populated with five caterpillars. Two maize leaf sections which had been immersed in a solution of active ingredient were also introduced. The first assessment was carried out after four hours. In the event that at least one caterpillar was still alive, a feed mix was added. The mortality was determined after 24 hours.

In this experiment, the active ingredients I-1 to I-7 and I-10, I -3[sic] showed limit concentrations of 0.04 to 0.2 ppm, while the comparison active ingredients A, B and C showed limit concentrations of over 0.2 ppm.

Example 3

Action Against *Nephotettix cincticeps* (Green Rice Leafhopper), Contact Action

Filter disks (Ø 9 cm) were treated with 1 ml of aqueous formulations of the active ingredient and subsequently populated with five adult leafhoppers. The mortality was determined after 24 hours.

In this experiment, the active ingredients I-3 and I-4 showed limit concentrations of 0.04 mg, while the comparison active ingredients A and B showed limit concentrations of 0.2 mg.

Example 4

Action Against *Nephotettix cincticeps* (Crop Spray Experiment)

Rice plants grown in pots (plant height approximately 8 cm) were sprayed to runoff point with aqueous formulations of active ingredients. After drying, the plants were populated with 20 adult leafhoppers. The mortality was determined after 24 hours.

In this experiment, the active ingredients I-3 and I-4 showed limit concentrations of 20 to 40 ppm, while the comparison active ingredients A and B showed limit concentrations of 400 ppm.

Example 5

Action Against *Tetranychus telarius**) (Red Spider Mite)

*) syn. urticae

Dwarf beans in pots which had developed the second true leaf pair were sprayed to runoff point with aqueous preparations of active ingredients. The plants were severely infested with adult mites and eggs. After 5 days in the greenhouse, the infestation level was determined by means of a stereomicroscope.

In this experiment, the active ingredients I-1 and I-3 to I-6 showed limit concentrations of 20 to 40 ppm, while the comparison active ingredients A, B and C showed limit concentrations of 100 ppm or more.

We claim:

1. A bisoxime ether compound of formula I

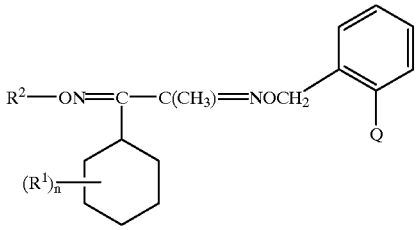

(I)

wherein $R^1$ is halogen, $C_1$–$C_4$-alkyl, $C_1$–$C_4$-haloalkyl, $C_1$–$C_4$-alkoxy or $C_1$–$C_4$-haloalkoxy;

n is 1 to 5, and the radicals $R^1$ are identical or different when n is other than 1;

$R^2$ is $C_1$–$C_4$-alkyl, $C_3$–$C_6$-alkenyl or $C_3$–$C_6$-alkynyl, and these groups are unsubstituted, partially halogenated or fully halogenated;

Q is C(=CHOCH$_3$)—COOCH$_3$, C(=CHCH$_3$)—COOCH$_3$, C(=NOCH$_3$)—COOCH$_3$ or C(=NOCH$_3$)—CONHCH$_3$;

or a salt thereof.

2. A process for the preparation of the compound of formula I defined in claim 1, which comprises reacting a benzyl compound of formula II

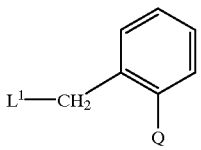

(II)

wherein $L^1$ represents a nucleophilically exchangeable leaving group, with a hydroxyimine of formula III

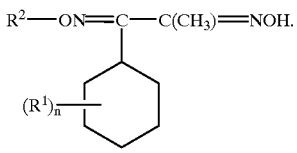

(III)

3. A process for the preparation of the compound of formula I defined in claim 1, which comprises reacting a benzyl compound of formula II

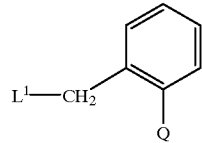

(II)

wherein $L^1$ represents a nucleophilically exchangeable leaving group, with a dihydroxyimine of formula IV

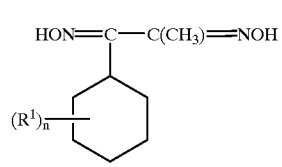

(IV)

to give a compound of formula V

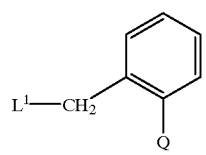

(V)

and subsequently reacting V with a compound of formula VI $R^2$—$L^2$ (VI)

wherein $L^2$ is a nucleophilically exchangeable leaving group, to give I.

4. A process for the preparation of the compound of formula I defined in claim 1, which comprises reacting a benzyl compound of formula II

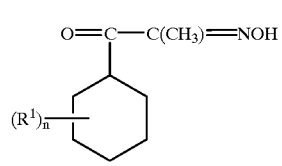

(II)

wherein $L^1$ represents a nucleophilically exchangeable leaving group, with a carbonylhydroxyimine of formula VII (VII)

O=C—C(CH$_3$)=NOH ($R^1$)$_n$ to give a compound of formula VIII

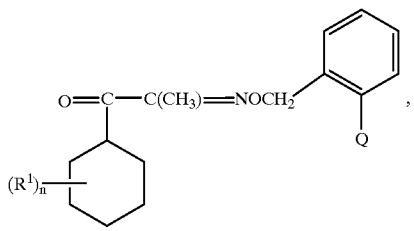
(VIII)

and subsequently reacting VIII either a) first with hydroxylamine or a salt thereof and then with a compound of formula VI

 (VI)

wherein $L^2$ is a nucleophilically exchangeable leaving group, or b) with a hydroxylamine or a hydroxylammonium salt of formula IXa or IXb

 IXb

 IXb where $Q^\ominus$ is the anion of an acid.

5. A composition for controlling animal pests or harmful fungi, comprising customary additives and an effective amount of the compound of formula I defined in claim 1.

6. The composition defined in claim 5, wherein the animal pests are from the classes of insects, arachnids and nematodes.

7. A method of controlling animal pests or harmful fungi, which comprises treating the pests or the harmful fungi, their environment or plants, areas, materials or spaces to be kept free from them with an effective amount of the compound of formula I defined in claim 1.

8. A compound of formula III

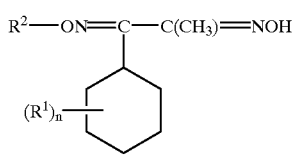
(III)

wherein $R^1$ is halogen, $C_1$–$C_4$-alkyl, $C_1$–$C_4$-haloalkyl, $C_1$–$C_4$-alkoxy or $C_1$–$C_4$-haloalkoxy;

n is 1 to 5, and the radicals $R^1$ are identical or different when n is other than 1; and $R^2$ is $C_1$–$C_4$-alkyl, $C_3$–$C_6$-alkenyl or $C_3$–$C_6$-alkynyl, and these groups are unsubstituted, partially halogenated or fully halogenated.

9. A compound of formula IV

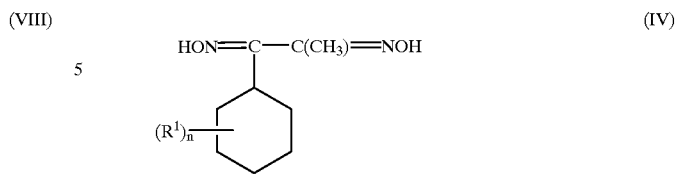
(IV)

wherein $R^1$ is halogen, $C_1$–$C_4$-alkyl, $C_1$–$C_4$-haloalkyl, $C_1$–$C_4$-alkoxy or $C_1$–$C_4$-haloalkoxy; and n is 1 to 5, and the radicals $R^1$ are identical or different when n is other than 1.

10. A compound of formula VII

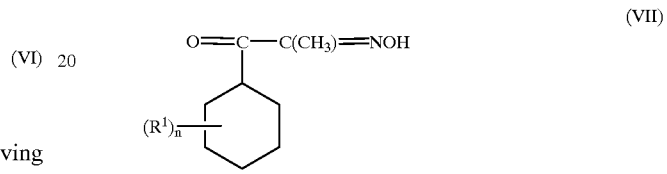
(VII)

wherein $R^1$ is halogen, $C_1$–$C_4$-alkyl, $C_1$–$C_4$-haloalkyl, $C_1$–$C_4$-alkoxy or $C_1$–$C_4$-haloalkoxy; and n is 1 to 5, and the radicals $R^1$ are identical or different when n is other than 1.

11. A compound of formula VIIa

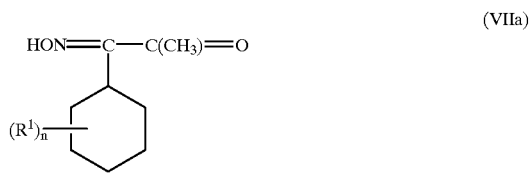
(VIIa)

wherein $R^1$ is halogen, $C_1$–$C_4$-alkyl, $C_1$–$C_4$-haloalkyl, $C_1$–$C_4$-alkoxy or $C_1$–$C_4$-haloalkoxy; and n is 1 to 5, and the radicals $R^1$ are identical or different when n is other than 1.

12. A compound of formula VIII

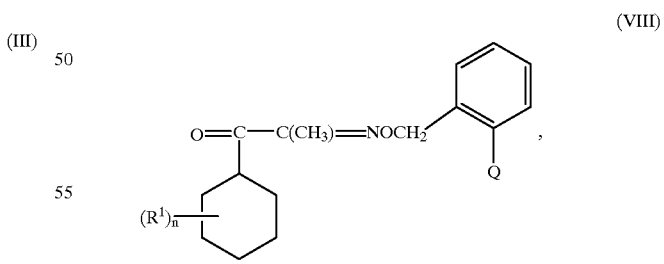
(VIII)

wherein $R^1$ is halogen, $C_1$–$C_4$-alkyl, $C_1$–$C_4$-haloalkyl, $C_1$–$C_4$-alkoxy or $C_1$–$C_4$-haloalkoxy;

n is 1 to 5, and the radicals $R^1$ are identical or different when n is other than 1; and Q is $C(=CHOCH_3)$—$COOCH_3$, $C(=CHCH_3)$—$COOCH_3$, $C(=NOCH_3)$—$COOCH_3$ or $C(=NOCH_3)$—$CONHCH_3$.

13. A compound of formula X

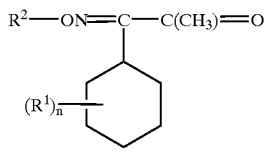
(X)

wherein
  $R^1$ is halogen, $C_1$–$C_4$-alkyl, $C_1$–$C_4$-haloalkyl, $C_1$–$C_4$-alkoxy or $C_1$–$C_4$-haloalkoxy;
  n is 1 to 5, and the radicals $R^1$ are identical or different when n is other than 1; and
  $R^2$ is $C_1$–$C_4$-alkyl, $C_3$–$C_6$-alkenyl or $C_3$–$C_6$-alkynyl, and these groups are unsubstituted, partially halogenated or fully halogenated.

14. A compound of formula XI

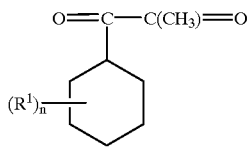
(XI)

wherein
  $R^1$ is halogen, $C_1$–$C_4$-alkyl, $C_1$–$C_4$-haloalkyl, $C_1$–$C_4$-alkoxy or $C_1$–$C_4$-haloalkoxy; and
  n is 1 to 5, and the radicals $R^1$ are identical or different when n is other than 1.

15. A compound of formula XIII

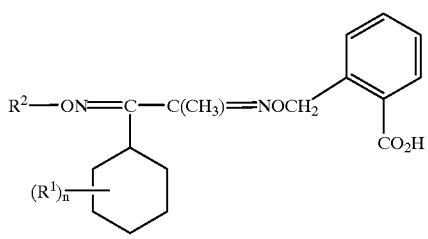
(XIII)

wherein
  $R^1$ is halogen, $C_1$–$C_4$-alkyl, $C_1$–$C_4$-haloalkyl, $C_1$–$C_4$-alkoxy or $C_1$–$C_4$-haloalkoxy;
  n is 1 to 5, and the radicals $R^1$ are identical or different when n is other than 1; and
  $R^2$ is $C_1$–$C_4$-alkyl, $C_3$–$C_6$-alkenyl or $C_3$–$C_6$-alkynyl, and these groups are unsubstituted, partially halogenated or fully halogenated.

16. A compound of formula XV

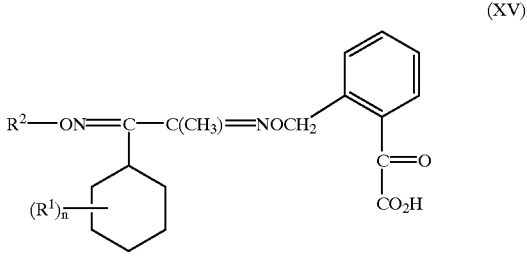
(XV)

wherein
  $R^1$ is halogen, $C_1$–$C_4$-alkyl, $C_1$–$C_4$-haloalkyl, $C_1$–$C_4$-alkoxy or $C_1$–$C_4$-haloalkoxy;
  n is 1 to 5, and the radicals $R^1$ are identical or different when n is other than 1; and
  $R^2$ is $C_1$–$C_4$-alkyl, $C_3$–$C_6$-alkenyl or $C_3$–$C_6$-alkynyl, and these groups are unsubstituted, partially halogenated or fully halogenated.

17. A compound of formula XVI

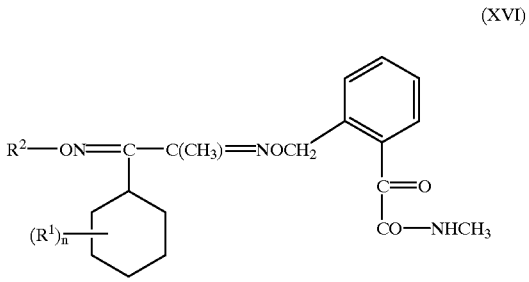
(XVI)

wherein
  $R^1$ is halogen, $C_1$–$C_4$-alkyl, $C_1$–$C_4$-haloalkyl, $C_1$–$C_4$-alkoxy or $C_1$–$C_4$-haloalkoxy;
  n is 1 to 5, and the radicals $R^1$ are identical or different when n is other than 1; and
  $R^2$ is $C_1$–$C_4$-alkyl, $C_3$–$C_6$-alkenyl or $C_3$–$C_6$-alkynyl, and these groups are unsubstituted, partially halogenated or fully halogenated.

* * * * *